United States Patent
Leemrijse et al.

(10) Patent No.: US 10,952,865 B2
(45) Date of Patent: Mar. 23, 2021

(54) ANKLE PROSTHESIS (71) Applicant: IN2BONES, Ecully (FR)

(72) Inventors: Thibaut Jean Pierre Henry Leemrijse, Brussels (BE); Pit Putzeys, Bridel (LU); Laurent François René Paul, Mellery (BE); Per-Henrik Agren, Stockholm (SE); Jean-Luc Pierre Marie Besse, Chaponnay (FR)

(73) Assignee: IN2BONES, Ecully (FR)

( * ) Notice: Subject to any disclaimer, the term of this patent is extended or adjusted under 35 U.S.C. 154(b) by 44 days.

(21) Appl. No.: 16/120,942

(22) Filed: Sep. 4, 2018

(65) Prior Publication Data
US 2019/0070012 A1 Mar. 7, 2019

(30) Foreign Application Priority Data
Sep. 5, 2017 (FR) ...................... 17 58185

(51) Int. Cl.
*A61F 2/42* (2006.01)
*A61F 2/30* (2006.01)

(52) U.S. Cl.
CPC ........ *A61F 2/4202* (2013.01); *A61F 2/30749* (2013.01); *A61F 2002/3021* (2013.01); *A61F 2002/30131* (2013.01); *A61F 2002/30205* (2013.01); *A61F 2002/30327* (2013.01); *A61F 2002/30387* (2013.01); *A61F 2002/30518* (2013.01); *A61F 2002/30621* (2013.01); *A61F 2002/30841* (2013.01);

(Continued)

(58) Field of Classification Search
None
See application file for complete search history.

(56) References Cited

U.S. PATENT DOCUMENTS 4,069,518 A * 1/1978 Groth, Jr. .............. A61F 2/4202
623/21.18
4,309,778 A * 1/1982 Buechel ................ A61F 2/3868
623/20.29

(Continued)

FOREIGN PATENT DOCUMENTS

FR 2905259 A1 3/2008
WO 2014149952 A1 9/2014

*Primary Examiner* — Bruce E Snow
*Assistant Examiner* — Melissa A Hoban
(74) *Attorney, Agent, or Firm* — Nath, Goldberg & Meyer; Jerald L. Meyer (57) ABSTRACT The invention concerns an ankle prosthesis (100), comprising a talar component (200) which includes a talar upper face (201) defining a first articular surface (202) and which extends between a talar anterior edge (203) and an opposite talar posterior edge (204) according to a first average direction, said first articular surface (202) being curved according to said first average direction, said first articular surface (202) comprising a first curved portion (202A) and a second curved portion (202B), each extending according to said first average direction, said first curved portion (202A) having a first curvature and said second curved portion (202B) having a second curvature, said prosthesis (100) being characterized in that said first curved portion (202A) and said second curved portion (202B) define respectively an anterior portion and a posterior portion of said first articular surface (202), said first curvature being greater than said second curvature.

20 Claims, 4 Drawing Sheets

(52) U.S. Cl.
CPC ............... *A61F 2002/30878* (2013.01); *A61F 2002/30934* (2013.01); *A61F 2002/4205* (2013.01); *A61F 2002/4207* (2013.01)

(56) References Cited

U.S. PATENT DOCUMENTS

| | | | | |
|---|---|---|---|---|
| 4,470,158 A * | 9/1984 | Pappas | ................... | A61F 2/3804 623/20.21 |
| 6,039,763 A * | 3/2000 | Shelokov | ............... | A61F 2/4425 623/17.16 |
| 6,183,519 B1 * | 2/2001 | Bonnin | ................. | A61F 2/4202 623/21.11 |
| 6,863,691 B2 * | 3/2005 | Short | ................... | A61F 2/4202 623/21.18 |
| 6,926,739 B1 * | 8/2005 | O'Connor | ............. | A61F 2/4202 623/20.29 |
| 7,615,082 B2 * | 11/2009 | Naegerl | ................ | A61F 2/4202 623/21.18 |
| 7,625,409 B2 * | 12/2009 | Saltzman | ............... | A61B 17/15 623/21.18 |
| 8,597,361 B2 * | 12/2013 | Sidebotham | .......... | A61F 2/4202 623/18.11 |
| 8,668,743 B2 * | 3/2014 | Perler | ................... | A61F 2/4202 623/21.18 |
| 8,690,956 B2 * | 4/2014 | Cook | ................... | A61F 2/4202 623/14.12 |
| 9,468,532 B2 * | 10/2016 | Perler | ................... | A61F 2/4202 |
| 9,877,839 B2 * | 1/2018 | Dhillon | ................. | A61F 2/4202 |
| 10,398,562 B2 * | 9/2019 | Valderrabano | ......... | A61F 2/4606 |
| 2005/0004676 A1 * | 1/2005 | Schon | ................... | A61B 17/15 623/21.18 |
| 2006/0142870 A1 * | 6/2006 | Robinson | ............... | A61B 17/15 623/21.18 |
| 2010/0004743 A1 * | 1/2010 | Strzepa | ................. | A61F 2/4202 623/14.12 |
| 2014/0135939 A1 * | 5/2014 | Petteys | ................. | A61F 2/4202 623/21.18 |
| 2014/0180427 A1 | 6/2014 | Harding, Jr. | | |
| 2015/0320567 A1 * | 11/2015 | Terrill | ................... | A61F 2/4202 623/21.18 |
| 2016/0008139 A1 * | 1/2016 | Siegler | ................. | A61F 2/4202 623/21.18 |
| 2018/0125663 A1 * | 5/2018 | Huxel | ....................... | A61F 2/46 |
| 2019/0070012 A1 * | 3/2019 | Leemrijse | ............ | A61F 2/4202 |

* cited by examiner

ANKLE PROSTHESIS

The invention relates to the general field of ankle prostheses, that is to say implantable devices intended for the replacement of ankle joints, in particular in the context of an orthopedic treatment.

The invention more specifically concerns an ankle prosthesis, comprising a talar component which includes a talar upper face defining a first articular surface and which extends between a talar anterior edge and an opposite talar posterior edge according to a first average direction, said first articular surface being curved according to said first average direction.

In order to treat some bone pathologies of the ankle, such as osteoarthritis, causing a degradation or disappearance of the articular cartilage, it is known to carry out an arthrodesis of the ankle joint. Such an arthrodesis operation aims to limit, or even totally block, the ankle mobility by osteosynthesis, in order to stop the joint pain felt by the patient. While the arthrodesis of the ankle joint is generally satisfactory, its main drawback lies specifically in the suppression of the mobility of the joint, which should then be compensated as much as possible by the other joints of the leg of the patient. A long adaptation period is then necessary for the patient to find back, after operation, satisfactory locomotion capabilities. Furthermore, the blocking of the ankle joint causes high mechanical stresses on the neighboring joints, which are then exposed to a high risk of early degeneration.

This is the reason why it has been proposed to proceed, in some cases, with an arthroplasty of the ankle as an alternative to arthrodesis, that is to say with the replacement of the damaged joint of the ankle by a prosthetic, artificial joint.

Thus, an ankle prosthesis formed by several components has been introduced, namely a talar component and a tibial component, respectively intended to be attached to the talus and tibia, and a plastic pad which, in turn, is intended to be interposed between the talar component and the tibial component and be articulated in contact with the talar component.

Unlike the conventional arthrodesis, the use of such a known prosthesis allows maintaining a good mobility of the ankle of the patient, thus facilitating walking, and preserving the different joints of the foot and the leg of the patient. However, it has been observed that such a known ankle prosthesis still remains perfectible, in particular in terms of reproducibility of the complex natural movements of the ankle and their amplitude.

The objects assigned to the present invention consequently aim at overcoming the different drawbacks previously listed and at proposing a new ankle prosthesis having improved kinematics, more respectful of the natural movements of the ankle, and promoting a return for the patient to an easy and comfortable locomotion.

Another object of the invention aims at proposing a new ankle prosthesis whose setup is fast, easy and particularly low-traumatic for the patient.

Another object of the invention aims at proposing a new ankle prosthesis, robust and resistant, and whose holding in the body of the patient is particularly reliable.

Another object of the invention aims at proposing a new ankle prosthesis whose manufacture is relatively easy.

Another object of the invention aims at proposing a new ankle prosthesis allowing reducing the cost of the surgical procedure for setting up the prosthesis.

Another object of the invention aims at proposing a new ankle prosthesis allowing reducing the risk to the health of the patient related to the setup of the prosthesis and to the therapy.

Another object of the invention aims at proposing a new ankle prosthesis allowing treating a bone pathology of the patient in a particularly effective and rapid manner.

The objects assigned to the invention are achieved using an ankle prosthesis comprising a talar component which includes a talar upper face defining a first articular surface and which extends between a talar anterior edge and an opposite talar posterior edge according to a first average direction, said first articular surface being curved according to said first average direction, said first articular surface comprising a first curved portion and a second curved portion, each extending according to said first average direction, said first curved portion having a first curvature and said second curved portion having a second curvature, said prosthesis being characterized in that said first curved portion and said second curved portion define respectively an anterior portion and a posterior portion of said first articular surface, said first curvature being greater than said second curvature.

Other particularities and advantages of the invention will appear and will come out in more details on reading the description made hereinafter, with reference to the appended drawings, given only as an illustrative and non-limiting example, in which.

Figure 1:
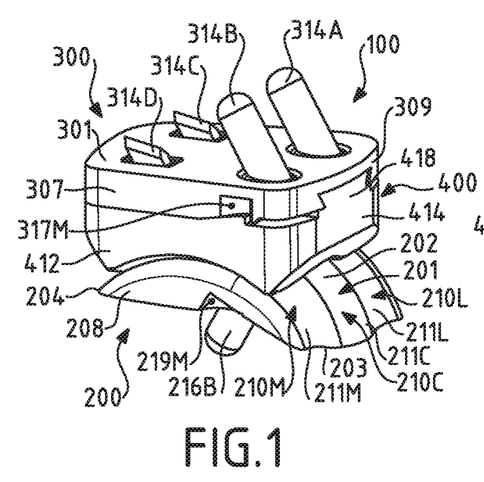
FIGS. 1 and 2 illustrate, in different perspective views, a preferred embodiment of the prosthesis according to the invention in which the prosthesis comprises, in addition to a talar component, a tibial component and an intermediate component.
Figure 2:
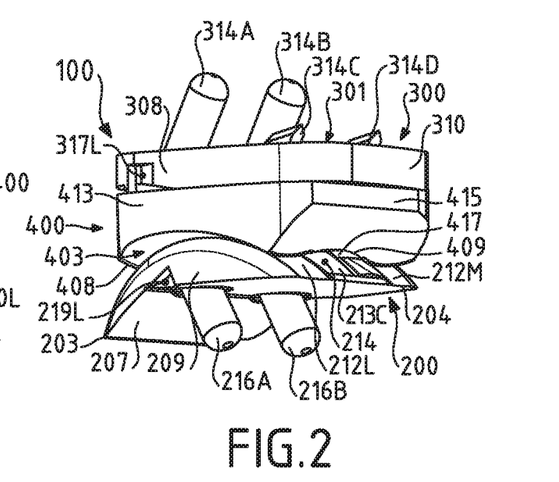

The invention concerns an ankle prosthesis 100, including a preferred embodiment illustrated in FIGS. 1 and 2. Said prosthesis 100 constitutes a device surgically implantable in the body of a human or animal patient, which is intended for the replacement of a given ankle joint. Advantageously, said prosthesis 100 is designed to totally replace the concerned ankle joint (total ankle prosthesis, TAP). As such, the prosthesis 100 according to the invention is designed to be inserted and interposed between a lower end of a tibia and a corresponding talus of a foot of a patient. Advantageously, the considered tibia and talus will be subjected, prior to the setup of the prosthesis 100 according to the invention in the body of the patient, to an adequate preparation, and for example an extraction of cartilage elements and bone sections, so as to remove all or part of the natural articular surfaces of the ankle joint to be replaced.

The prosthesis 100 illustrated as an example in FIGS. 1 to 5 is intended to be set up at the level of a left foot of a patient. Of course, the invention also covers a prosthesis which would be intended to be set up at the level of a right foot of the patient. Advantageously, said prosthesis would be defined by symmetry, relative to the sagittal plane of the patient, of the prosthesis 100 illustrated in the Figures.

In accordance with the invention, said prosthesis 100 comprises a talar component 200, including a preferred embodiment which is illustrated in FIGS. 6 to 10, and which is advantageously intended to be related to the talus of a foot of a patient. The talar component 200 includes a talar upper face 201, which defines a first articular surface 202 of the prosthesis 100. As illustrated, said talar upper face 201 extends between a talar anterior edge 203 and an opposite talar posterior edge 204 according to a first average direction A-A' and, preferably, between a talar lateral edge 205 and an opposite talar medial edge 206 according to a second average direction B-B', orthogonal to said first average direction A-A'. Advantageously, said first average direction A-A' might correspond to a first average antero-posterior direction in normal use of the prosthesis 100. Said second average direction B-B' might then advantageously correspond to a first average latero-medial direction. Advantageously, said talar lateral edge 205 and said talar medial edge 206 are rounded, chamfered.

It should be noted here that the terms <<posterior>>, <<anterior>>, <<medial>> and <<lateral>> are preferably used in the present description to qualify elements or features in connection with their respective orientation relative to the body of the patient, in normal use of the prosthesis 100. Thus, the term <<medial>> is preferably used to refer to an element of the prosthesis 100 which is intended to be positioned and oriented on the side closest to the midsagittal axis (or median axis) of the body of the patient, in other words, the side oriented towards the inside of the foot and leg of the patient. In contrast, the term <<lateral>> is used in connection with the side farthest from the midsagittal axis. Following the same logic, the terms <<posterior>> and <<anterior>>, preferably refer to a rearward, respectively forward, positioning relative to the frontal plane of the patient.

According to the preferred embodiment illustrated in the figures, the talar component 200 also includes a talar lower face 207, opposite to said talar upper face 201, and which is advantageously connected to the latter at the level of said talar anterior edge 203 and talar posterior edge 204. Said talar lower face 207 is preferably intended to be positioned in contact in or on an area of the talus of the patient specially prepared beforehand. Preferably, the talar lower face 207 is defined by first and second substantially planar contiguous portions (FIG. 7), which extend generally according to respective secant planes, for example at an elevation angle of 30° of the first planar portion relative to the second planar portion. The first planar portion preferably forms an anterior portion of the talar lower face 207, whereas the second planar portion, which extends according to a substantially horizontal plane in normal use of the prosthesis 100 according to the invention, advantageously forms a both central and posterior portion of the talar lower face 207. A fillet may be provided at the junction of said first and second planar portions. Such a particularly simple design of the talar lower face 207 limits the number and the complexity of the bone sections (in this instance, two) necessary to the prior preparation of the talus and facilitates the setup of the talar component 200 in the body of the patient.

As illustrated, the talar component 200 may also include a talar medial face 208 and an opposite talar lateral face 209, which connect respectively the talar medial edge 206 and the talar lateral edge 205 to said talar lower face 207. Preferably, said talar medial face 208 and talar lateral face 209 are generally bulged outwardly from the talar component 200, in order to respect at best the natural anatomical conformation of the area of the talus at the level of which the talar component 200 is intended to be set up.

Preferably, the prosthesis 100 according to the invention comprises a tibial component 300 (FIGS. 11 to 15), intended to be related to a lower end of the tibia of the patient. Said tibial component 300 includes a tibial upper face 301 and an opposite tibial lower face 302. As illustrated, said tibial lower face 302 preferably extends, on the one hand, between a tibial anterior edge 303 and an opposite tibial posterior edge 304, preferably according to a third average direction C-C' and, on the other hand, between a tibial lateral edge 305 and an opposite tibial medial edge 306, preferably according to a fourth average direction D-D', orthogonal to said third average direction C-C'.

Advantageously, said third average direction C-C' may correspond to a second average antero-posterior direction in normal use of the prosthesis 100. Said fourth average direction D-D' may then advantageously correspond to a second average latero-medial direction. Said second average antero-posterior direction and second average latero-medial direction of the tibial component 300 are advantageously respectively parallel to said first average antero-posterior direction and first average latero-medial direction of the talar component 200, in normal use of the prosthesis 100.

In the preferred embodiment illustrated in the figures, the tibial upper face 301 and the tibial lower face 302 extend respectively according to substantially parallel average extension planes, said tibial component 300 being in the general form of a plate. Said tibial upper face 301 is preferably intended to be positioned in contact in or on an area of the tibia specially prepared beforehand. As illustrated, the tibial component 300 may also include a tibial medial face 307 and an opposite tibial lateral face 308, which connect respectively the tibial medial edge 306 and the tibial lateral edge 305 to said tibial upper face 301. Advantageously, said tibial medial edge 306 is substantially rectilinear and said tibial medial face 307 is substantially planar (FIGS. 11 to 14), so that the surgeon could accurately position said tibial component 300 in the body of the patient, by aligning said tibial medial face 307 along a rectilinear section made at the level of the inner malleolus. This advantageously allows reducing the areas of uncovered bone sections, which might promote the appearance of *geodes* or cysts. Furthermore, the tibial component 300 may include a tibial anterior face 309 and an opposite tibial posterior face 310, which in turn connect respectively the tibial anterior edge 303 and the tibial posterior edge 304 to said tibial upper face 301.

Preferably, said talar component 200 and/or said tibial component 300 form respectively a one-piece part made of a biocompatible and wear-resistant material. Advantageously, said talar component 200 and/or said tibial component 300 are made of a metal material, for example of a chromium-cobalt alloy CrCo, of stainless steel or still of titanium. According to a variant, said talar component 200 and said tibial component 300 respectively consist of a cast part. According to an alternative variant, said talar component 200 and said tibial component 300 respectively consist of a machined part. Of course, other suitable materials might be considered, such as for example a ceramic material, as well as other manufacturing processes (by injection, molding, sintering, etc.).

Advantageously, the talar lower face 207 of the talar component 200 and/or the tibial upper face 301 of the tibial component 300 might be provided with a particular surface coating (for example made of porous titanium or of hydroxyapatite), or might have been subjected to a particular mechanical processing (sanding, grooving, etc.), in order to promote the bone hooking of the talar component 200 to the talus and/or the tibial component 300 to the corresponding tibia.

Preferably, the prosthesis 100 according to the invention also comprises an intermediate component 400 (or pad, or still insert) (FIGS. 16 to 19), which is designed to be interposed between said talar component 200 and said tibial component 300, as illustrated as an example in FIGS. 1 to 5.

Said intermediate component 400 comprises an intermediate upper face 401, preferably intended to come into contact with the tibial lower face 302 of the tibial component 300, and an opposite intermediate lower face 402, which in turn is preferably intended to come into contact with the talar upper face 201 of the talar component 200. Said intermediate lower face 402 advantageously defines a second articular surface 403 of the prosthesis 100, designed to cooperate with said first articular surface 202 defined by the talar upper face 201 of the talar component 200.

Preferably, said intermediate upper face 401 extends, on the one hand, between a first intermediate anterior edge 404 and a first opposite intermediate posterior edge 405 (for example according to a fifth average direction E-E') and, on the other hand, between a first intermediate lateral edge 406 and a first opposite intermediate medial edge 407 (for example according to a sixth average direction F-F', orthogonal to said fifth average direction E-E'). Said intermediate lower face 402 in turn extends preferably, on the one hand, between a second intermediate anterior edge 408 and an opposite second intermediate posterior edge 409, according to said fifth average direction E-E' and, on the other hand, between a second intermediate lateral edge 410 and an opposite second intermediate medial edge 411, according to said sixth average direction F-F'. Said second intermediate anterior edge 408 and said second intermediate posterior edge 409 may be advantageously chamfered, as illustrated, in order to limit the risks of irritation or damage of the surrounding soft tissues, when the prosthesis 100 is in use.

The intermediate component 400 may also include an intermediate medial face 412 and an opposite intermediate lateral face 413, which connect respectively the first intermediate medial edge 407 and the first intermediate lateral edge 406 to said intermediate lower face 402. Advantageously, the intermediate medial face 412 is substantially planar, for reasons substantially identical to those set out hereinbefore in connection with the tibial medial face 307 of the tibial component 300, whereas the intermediate lateral face 413 may be generally bulged, with a concavity oriented towards said intermediate medial face 412. Furthermore, the intermediate component 400 may include an intermediate anterior face 414 and an opposite intermediate posterior face 415, which in turn connect respectively the first intermediate anterior edge 404 and the first intermediate posterior edge 405 to said intermediate lower face 402.

Figure 3:
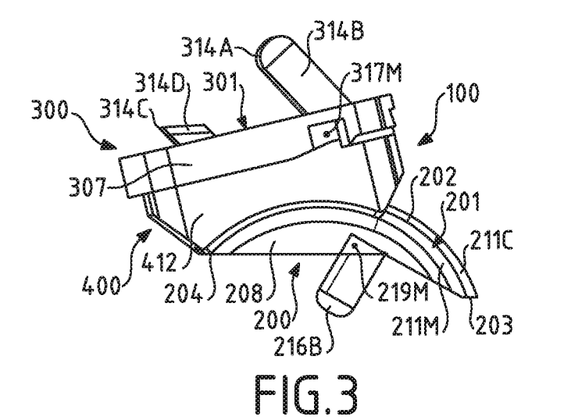
FIGS. 3 to 5, illustrate, in medial views, three spatial configurations that the prosthesis of FIGS. 1 and 2 is likely to adopt according to the relative orientation of the left foot and tibia of a patient, namely respectively at a plantar flexion position (FIG. 3), a so-called neutral position (FIG. 4) and a dorsal flexion position (FIG. 5)
Figure 4:
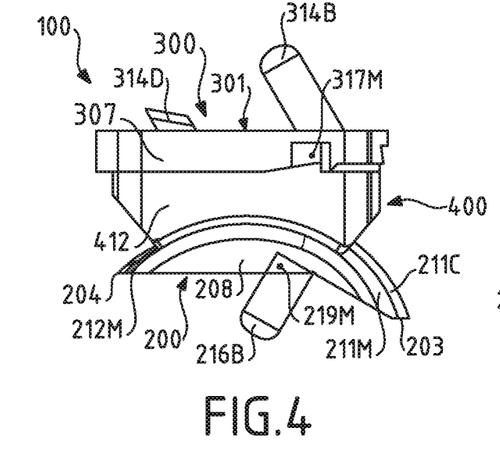
Figure 5:
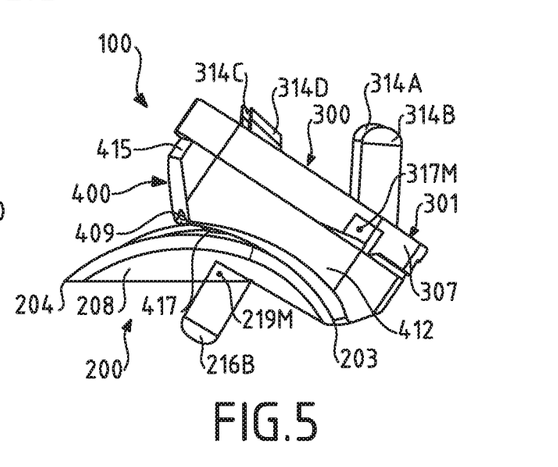

As illustrated in FIGS. 3 to 5, the intermediate component 400 is likely to be displaced by sliding in contact on the talar component 200 along an average antero-posterior direction and, in particular, according to a generally postero-anterior pathway (that is to say from the rear to the front) between the talar posterior edge 204 (plantar flexion, FIG. 3) and the talar anterior edge 203 (dorsal flexion, FIG. 5), passing through a so-called neutral intermediate position (FIG. 4), according to the inclination affected by the foot of the patient relative to the tibia thereof.

Preferably, said intermediate component 400 is a one-piece part made of a material having a low friction coefficient, for example a plastic material such as a high-density polyethylene (HDPE). It may, for example, consist of a machined or molded part.

Alternatively, the prosthesis 100 may comprise no intermediate component 400, the tibial lower face 302 might then be designed to define on its own, a second articular surface intended to cooperate directly with the first articular surface 202 defined by the talar upper face 201 of the talar component 200.

Figure 6:
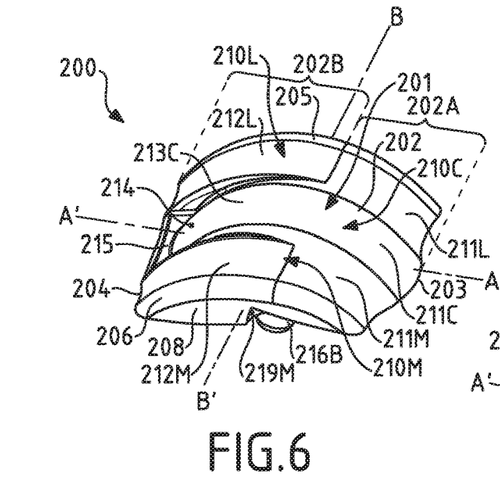
FIGS. 6 and 7 illustrate, respectively according to top and bottom perspective views, the talar component of the prosthesis of FIGS. 1 and 2.

According to the invention, and as shown in particular in FIG. 6, said first articular surface 202 is curved, bulged, according to said first average direction A-A'. Conversely, the second articular surface 403 defined by the intermediate lower face 402 of the talar component 400 is preferably curved according to said fifth average direction E-E'. Said first articular surface 202 is preferably generally convex (that is to say with a concavity oriented towards the talar lower face 207 of the talar component 200), whereas the second articular surface 403 is generally concave. According to an alternative variant (not illustrated), a reversed configuration might be considered without departing from the scope of the invention, the first articular surface 202 being generally concave, whereas the second articular surface 403 is generally convex.

Advantageously, said first articular surface 202 (and, preferably, said second articular surface 403) has(have) more specifically (each) the general average shape of a substantially frustoconical (fictional) surface fraction, derived from a fictional cone, which surface is preferably oriented so that its large base is oriented towards the outer malleolus and that its small base is oriented towards the inner malleolus of the considered foot. Thus, when the intermediate component 400 is displaced in frictional contact relative to the talar component 200, by cooperation of said first 202 and second 403 articular surfaces, the intermediate component 400 does not describe a strictly antero-posterior or postero-anterior trajectory, but on the contrary a more or less curved trajectory. The foot of the patient is thus advantageously guided on the lateral side (medio-lateral direction) in dorsal flexion and, conversely, on the medial side (latero-medial-direction) in plantar flexion. Thus, the natural physiological kinematics of the joint of the ankle are best reproduced.

Alternatively, said first 202 and second 403 articular surfaces might have each the average general shape of a cylindrical (fictional) surface fraction, so as to define, on the contrary, articular kinematics in which the intermediate component 400 is displaced according to a substantially antero-posterior or postero-anterior trajectory.

According to the invention, said first articular surface 202 comprises at least two distinct curved surface portions, namely at least one first curved portion 202A and one second curved portion 202B, each extending according to said first average direction A-A', aligned one behind the other according to said first average direction A-A', said first curved portion 202A having a first curvature and said second curved portion 202B having a second curvature, according to said first average direction A-A'.

Thus, when viewed in section in a plane parallel to said first average direction A-A' and orthogonal to said second average direction B-B' (FIG. 10), said first articular surface 202 is described by at least two distinct curvilinear portions (respectively referred to in FIG. 10 by the same references 202A and 202B as for the corresponding first and second curved portions), preferably each forming an arc whose concavity is preferably directed towards the talar lower face 207, said curvilinear portions having (possibly average) centers of curvature distinct from each other.

According to a preferred variant, the first 202A and second 202B curved portions of the first articular surface 202 are respectively generally similar to first and second substantially frustoconical (fictional) surface fractions, said first and second surface fractions being preferably respectively derived from first and second virtual fictional cones having respectively first and second axes of rotation. Advantageously, the value of the half-angle at the apex of each of said first and second fictional cones is 8°. The choice of this particular configuration contributes to best reproducing the natural kinematics of the anatomical ankle.

Alternatively, said first 202a and second 202b curved portions of the first articular surface 202 might be respectively generally similar to first and second substantially cylindrical surface fractions, said first and second surface fractions being preferably respectively derived from first and second fictional cylinders, having respectively first and second axes of rotation.

In other words, if said first articular surface 202 has, as previously stated, the average general shape of a substantially frustoconical (fictional) surface fraction of a fictional (or cylindrical) cone, this average general shape is more specifically defined, within the meaning of the invention, by the combination of at least first and second distinct fractions of substantially frustoconical (or cylindrical) surfaces. Each of these substantially frustoconical surfaces is preferably oriented so that its large base is oriented towards the outer malleolus and that its small base is oriented towards the inner malleolus of the considered foot. Thus, the first frustoconical surface fraction corresponding to the first curved portion 202A has a radius of curvature which varies, in a latero-medial direction of said second average direction B-B', decreasingly between a large radius of curvature $R_1$ and a small radius of curvature $r_1$. The second frustoconical surface fraction, corresponding to the second curved portion 202B, has in turn a radius of curvature which varies, in a latero-medial direction of said second average direction B-B', decreasingly between a large radius of curvature $R_2$ and a small radius of curvature $r_2$.

Alternatively, in the case where said first 202A and second 202B curved portions are generally similar to first and second substantially cylindrical surface fractions, said fractions might respectively have a radius of curvature $R'_1$, $R'_2$ which is constant according to said second average direction B-B'.

In accordance with the invention, said first and second curvatures are different, such that one of said first 202A and second 202B curved portions is therefore more curved, that is to say more strongly curved, than the other.

According to the preferred embodiment, considered hereinbefore, in which said first 202A and second 202B curved portions of the first articular surface 202 are respectively generally similar to first and second substantially frustoconical (fictional) surface fractions, such a difference in curvature may result in the fact that the first frustoconical surface fraction has a large radius of curvature $R_1$ and a small radius of curvature $r_1$ which are respectively different from the respective large radius of curvature $R_2$ and small radius of curvature $r_2$ of the second frustoconical surface fraction ($R_1 \neq R_2$ and $r_1 \neq r_2$). According to the alternative variant in which said first 202A and second 202B curved portions are respectively generally similar to first and second substantially cylindrical surface fractions, such a difference in curvature may result in the fact that the first cylindrical surface fraction has a radius of curvature $R'_1$ different from the respective radius of curvature $R'_2$ of the second cylindrical surface fraction.

As a result, the first articular surface 202 defined by the talar upper face 201, does not advantageously have the exact and perfect shape of a frustoconical (or cylindrical, as alternatively considered hereinbefore) surface portion, but it includes, on the contrary, a particular localized variation in its average general curvature according to said first average direction A-A'. The general kinematics of the prosthesis 100 are then not defined by a single rotation, but by at least two rotations at different radii, corresponding to at least two spatial configurations of the foot relative to the tibia. It is thus possible to generate a complex articular movement, with differentiated axes of rotation of the prosthetic joint between a plantar flexion position and a dorsal flexion position, and to approach even more faithfully the natural kinematic behavior of an anatomical ankle.

In the preferred embodiment illustrated in the figures, said first curved portion 202A and said second curved portion 202B define (or at least partially contribute to defining) respectively an anterior portion and a posterior portion of said first articular surface 202. As such, said first curved portion 202A preferably extends between the talar anterior edge 203 and the talar posterior edge 204 of the talar upper face 201 of the talar component 200, and more preferably, from said talar anterior edge 203 (or at least from the immediate vicinity of the latter) towards said talar posterior edge 204. Said second curved portion 202B then extends respectively between said first curved portion 202A and said talar posterior edge 204. Still preferably, said second curved portion 202B is contiguous to said first curved portion 202A and extends the latter up to said talar posterior edge 204 (or at least up to the immediate vicinity of the latter). The first curved portion 202A and the second curved portion 202B are thus aligned one behind the other according to the first average direction A-A', the first curved portion 202A (anterior portion) being positioned before the second curved portion 202B (posterior portion). Thus, when viewed in section in a plane parallel to the first average direction A-A' and orthogonal to the second average direction B-B' (FIG. 10), said first articular surface 202 is described by at least two distinct and preferably abutted curvilinear portions, each preferably forming an arc, and preferably connecting the talar anterior edge 203 to the talar posterior edge 204.

Said first curved portion 202A then advantageously corresponds to a portion of the first articular surface 202 with which the second articular surface 403 of the intermediate component 400 will cooperate, in dorsal flexion configuration of the foot of the patient (FIG. 5), whereas said second curved portion 202 corresponds to another portion of the first articular surface 202 with which said second articular surface 403 of the intermediate component 400 will cooperate, in plantar flexion configuration of the foot of the patient (FIG. 3).

Advantageously, said first and second curvatures, as well as the relative positioning of said first and second axes of rotation, will be selected such as to ensure a regular and harmonious transition between said first 202A and second 202B curved portions of the first articular surface 202.

Preferably, said first and second substantially frustoconical surface fractions join together in a contact plane inclined at an angle comprised between 10° and 30°, and preferably about 20°, towards said talar anterior edge 203 relative to a vertical plane containing said second axis of rotation, said contact plane containing said first and second axes of rotation. Indeed, it has been observed that an excellent tradeoff between the increase in the imparted angular displacement and the intrinsic stability of the prosthesis is thus obtained.

Preferably, said first curvature of the first curved portion 202A is greater than said second curvature of the second curved portion 202B, that is to say that said first curved portion 202A of the first articular surface 202 affects, in the first average direction A-A', a greater curvature than the respective one of said second curved portion 202B of the first articular surface 202 ($R_1 < R_2$ and $r_1 < r_2$, or $R'_1 < R'_2$).

In the aforementioned preferred case where said first 202A and second 202B curved portions define respectively an anterior portion and a posterior portion of the first articular surface 202, said first articular surface 202 has thus advantageously a more pronounced curvature in its anterior portion than in its posterior portion. Such a configuration is particularly interesting because it allows enabling the patient a dorsal flexion with a greater angular displacement, yet without the talus of the patient being deported in an anteroposterior direction, that is to say rearwards. Equipped with the prosthesis 100 according to the invention, the patient may thus bend his foot more easily, for example during the walking phase where the foot leaves the ground at the end of a step, or when he seeks to climb the steps of a staircase.

Preferably, said first curvature is constant or variable (according to the first average direction A-A'), whereas said second curvature is constant (according to the first average direction A-A'). Such a first variable curvature may advantageously correspond to a particular embodiment according to which the general form of the first curved portion 202A in turn is generally defined by the combination of a plurality of n distinct surface fractions substantially frustoconical or cylindrical (and not only by the aforementioned first fraction), which fractions would have different small rn and large Rn radii of curvature (or radii R'n) (and therefore different nth curvatures), advantageously decreasing according to said first average direction A-A'.

In the preferred case where the first curved portion 202A defines an anterior portion of the first articular surface 202 and where said nth curvatures vary increasingly towards the tibial anterior edge 203, the implementation of such a first variable curvature advantageously allows further improving the amplitude of the angular displacement offered by the prosthesis 100 in dorsal flexion.

The intra-articular forces, likely to exert at the interface of the first 202 and second 403 articular surfaces, being more significant in the plantar flexion phase than in the dorsal flexion phase, said second curved portion 202B is preferentially designed and dimensioned such that it advantageously has a surface area larger than the respective surface area of said first curved portion 202A. Thus, a better recovery of the intra-articular forces in plantar flexion is ensured, which allows improving the stability as well as the service life of the prosthesis 100.

Preferably, the first articular surface 202 forms a prosthetic bicondylar surface, and comprises:
a talar lateral area 210L, which extends between said talar anterior edge 203 and said talar posterior edge 204 according to said first average direction A-A', and between said talar lateral edge 205 and said talar medial edge 206 according to said second average direction B-B', and
a talar medial area 210M, which extends between said talar anterior edge 203 and said talar posterior edge 204 according to said first average direction A-A', and between said talar lateral area 210L and said talar medial edge 206 according to said second average direction B-B'.

Figure 8:
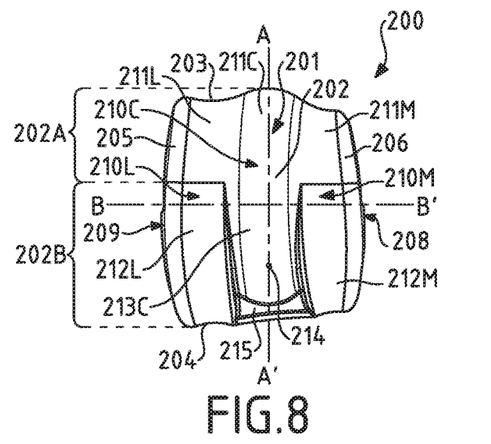
FIGS. 8 and 9 illustrate, respectively in top view and in bottom view, the talar component of FIGS. 6 and 7.

Still preferably, as illustrated in particular in FIGS. 6 and 8, said talar lateral area 210L and talar medial area 210M extend respectively from said talar anterior edge 203 (or at least from the immediate vicinity of the latter) up to said talar posterior edge 204 (or at least from the immediate vicinity of the latter). Said talar lateral area 210L then comprises a first lateral region 211L of said first curved portion 202A and a second lateral region 212L of said second curved portion 202B. Said talar medial area 210M comprises respectively a first medial region 211M of said first curved portion 202A and a second medial region 212M of said second curved portion 202B. As illustrated in the Figures, the second lateral region 212L and the second medial region 212M then extend preferably respectively said first lateral regions 211L and first medial region 211L, according to the first average direction A-A'. Advantageously, said talar lateral area 210L and talar medial area 210M thus form respectively, continuous lateral and medial prosthetic condyl portions according to the first average direction A-A'.

Advantageously, said first articular surface 202 also comprises a talar central area 210C, which is interposed between said talar lateral area 210L and said talar medial area 210M. As illustrated in the figures, said talar central area 210C extends, according to said first average direction A-A', from said talar anterior edge 203 (or at least from the immediate vicinity of the latter) towards the talar posterior edge 204, and advantageously comprises a first central region 211C of said first curved portion 202A.

In a particularly advantageous manner, said talar central area 210C also comprises a second curved central region 213C which extends said first central region 211C towards the talar posterior edge 204. However, said second central region 213C preferably does not constitute, as such, a central region of the second curved portion 202B. Indeed, said second central region 213C advantageously has a third curvature, according to the first average direction A-A', which is different from said second curvature of the second curved portion 202B. Said second curved portion 202B is then discontinuous according to the second average direction B-B'. In this instance, and in particular according to the preferred embodiment illustrated in the figures in which the first curvature of the first curved portion 202A is greater than the second curvature of the second curved portion 202B, said third curvature of the second central region 213C is advantageously greater than said second curvature. Thus, the second central region 213C is therefore more strongly curved than the surrounding second lateral region 212L and second medial region 212M. For example, said third curvature may be identical to said first curvature, the second central region 213C lying in the continuity of the first central region 211C.

As shown in particular in FIGS. 6 and 8, said second central region 213C then advantageously materializes a posterior central depression 214 in the average envelope of said first articular surface 202. Furthermore, said talar central area 210C of the first articular surface 202 may not extend up to the talar posterior edge 204 of the talar upper surface 201. The space thus formed between said talar central area 210C and said talar posterior edge 204 may be left free or, on the contrary, be preferably filled by a complementary portion 215 of a solid, and for example planar, talar upper face 201, so as to avoid the formation of an uncovered bone section area.

According to the preferred embodiment illustrated in the figures, said second articular surface 403, which is defined by the intermediate lower face 402 of the intermediate component 400, advantageously comprises an intermediate lateral area 416L, an intermediate medial area 416M, and also preferably an intermediate central area 416C, the latter being interposed between the two previous areas.

Each extending between said second intermediate anterior edge 408 and second intermediate posterior edge 409 according to said fifth average direction E-E', said intermediate lateral area 416L, intermediate medial area 416M and intermediate central area 416C are respectively intended to cooperate with said talar lateral area 210L, talar medial area 210M and talar central area 210C of said first articular surface 202. Preferably, said intermediate lateral area 416L and intermediate medial area 416M advantageously have, according to said fifth average direction E-E', curvatures respectively matching with the curvatures of said second lateral region 212L and second medial region 212M of the second curved portion 202B of said first articular surface 202. Said intermediate central area 416C advantageously has, in turn, according to said fifth average direction E-E', a curvature matching with the curvature of said first central region 211C of the first curved portion 202A of said first articular surface 202.

Figure 7:
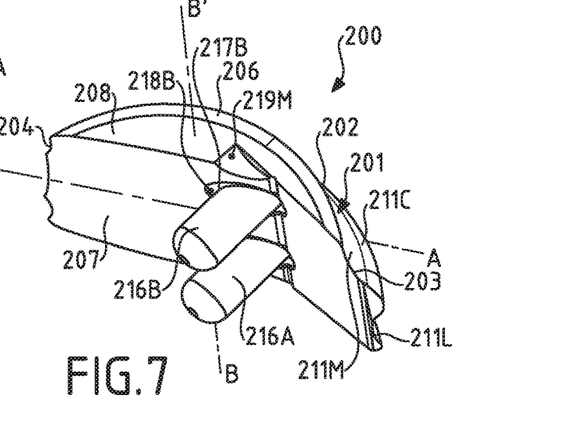
Figure 17:
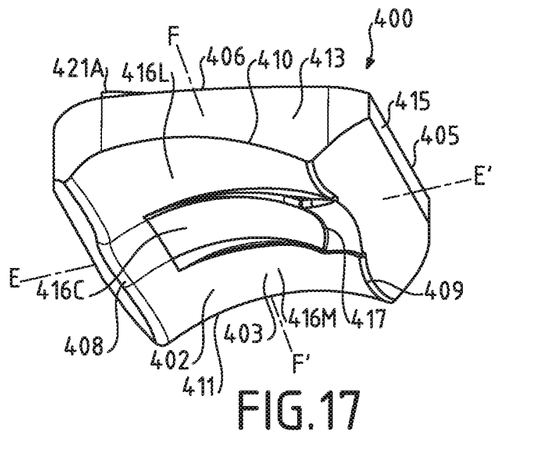

Preferably, and as shown in particularly in FIGS. 6 to 8, said talar central area 210C has a convex curvature according to said second average direction B-B', said talar lateral area 210L and talar medial area 210M respectively having a concave curvature according to said second average direction B-B'. Conversely, the intermediate lateral area 416L and the intermediate medial area 416M are advantageously convex according to said sixth average direction F-F', whereas the intermediate central area 416C is concave according to this same direction F-F' (FIG. 17).

Thus, in the plantar flexion position (FIG. 3) of the foot of the patient, said intermediate lateral area 416L and intermediate medial area 416M may advantageously rest respectively in a surface contact against said second lateral region 212L and second medial region 212M of the second curved portion 202B of the first articular surface 202.

In the dorsal flexion position (FIG. 5), said intermediate central area 416C may advantageously rest in surface contact with the first central region 211C of the first curved portion 202A of the first articular surface 202.

However, said intermediate lateral area 416L and intermediate medial area 416M may not then, preferably, rest in surface contact against said first lateral region 211L and first medial region 211M of the first curved portion 202A of the first articular surface 202 due to their respective different curvatures.

Thus, the cooperation of said first and second articular surfaces is advantageously not perfectly congruent. In the dorsal flexion position, the intermediate component 400 advantageously remains free to slightly slide and tilt, in a lateral or in a medial fashion, about an equilibrium position. In the case of a lateral tilting, the intermediate lateral area 416L of the second articular surface 403 may advantageously come into linear contact against the first lateral region 211L of the first curved portion 202A of the first articular surface 202 defined by the talar upper face 201 of the talar component 200. Conversely, in the case of a medial tilting, the intermediate medial area 416M of said second articular surface 403 may advantageously come into linear contact against the first medial region 211M of the first curved portion 202A of the first articular surface 202. Furthermore, in dorsal flexion position, the intermediate component 400 then advantageously has some limited latitude of rotation about a vertical axis.

By thus allowing the intermediate component 400 to maintain a slight mobility in translation in a medio-lateral direction and in rotation according to a vertical axis, such a configuration advantageously contributes to limiting the risks of loosening of the talar 200 and tibial 300 components under the effect of mechanical stresses which are exerted on the prosthesis 100, in normal use of the latter. Also, such a configuration advantageously allows compensating, to a certain extent, a slight relative positioning defect of the talar 200 and tibial 300 components, which contributes to facilitating the setup of the prosthesis 100 by the surgeon in the body of the patient.

Since the intermediate central area 416C preferably has, in accordance with the foregoing, a curvature greater than the respective curvatures of the intermediate lateral area 416L and intermediate medial area 416M, it may then define, in the vicinity of the second intermediate posterior edge 409, a protrusion 417 protruding from the surface of the intermediate lower face 402 (FIG. 17). In order to avoid any mechanical interaction between said protrusion 417 and the first articular surface 202, said posterior central depression 214 (materialized by the second central region 213C of the talar central area 210C, as mentioned hereinbefore) is advantageously left empty. Thus, in the plantar flexion position, said protrusion 417 may advantageously fade in said posterior central depression 214.

According to a variant (not illustrated in the figures), said tibial component 300 is designed to be movable relative to said intermediate component 400, said tibial 300 and intermediate 400 components being then preferably not mechanically interconnected. In this case, said tibial lower face 302 and said intermediate upper face 401 are preferably substantially planar and smooth, so that the tibial component 300 and the intermediate component 400 could come into planar surface contact against each other. In normal use of the prosthesis 100, the tibial component 300 and the intermediate component 400 are thus in contact against each other, and are movable relative to each other according to three degrees of freedom, namely according to a translation along an antero-posterior average direction, a translation along a medio-lateral average direction, and a rotation about an axis orthogonal to the contact plane of said tibial lower face 302 and intermediate upper face 401 therebetween.

According to another variant, illustrated in FIGS. 1 to 5, said tibial component 300 is designed to be fastened, that is to say secured, to said intermediate component 400, so as to advantageously suppress any degree of freedom between the tibial component 300 and the intermediate component 400. Such a securing of the latter advantageously allows improving the stability of the prosthetic joint. Preferably, said tibial component 300 and intermediate component 400 are designed to be fastened to each other using respective first and second complementary securing elements, more preferably according to a dovetail assembly.

Figure 16:
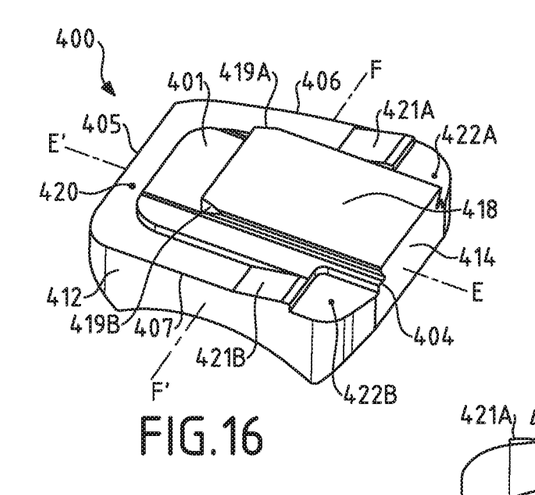
FIGS. 16 and 17 illustrate, respectively according to top and bottom perspective views, the intermediate component of the prosthesis of FIGS. 1 and 2.
Figure 18:
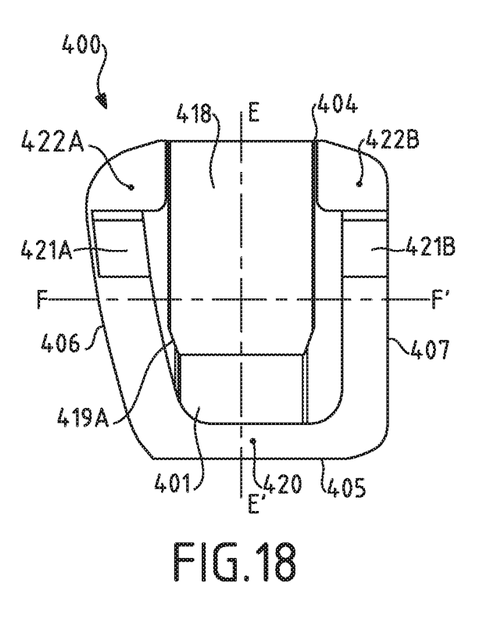
FIGS. 18 and 19 illustrate, respectively, in top and bottom views, the intermediate component of FIGS. 16 and 17.
Figure 19:
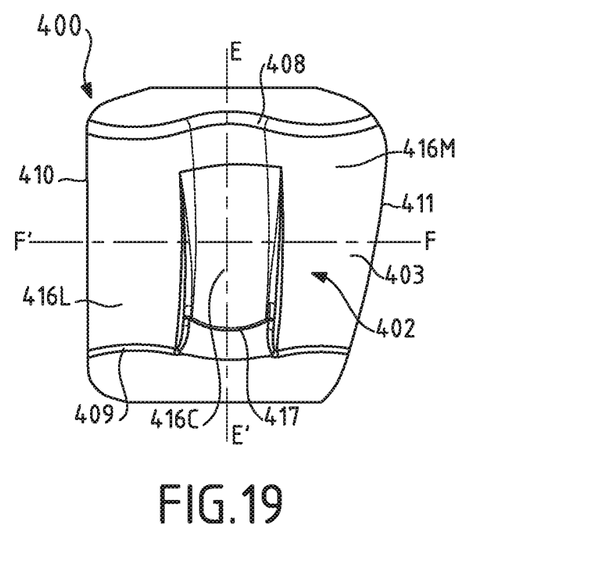

According to the preferred embodiment illustrated in the figures, the tibial lower face 302 of the tibial component 300 is thus advantageously provided with a groove 311, for example having a trapezoidal section, which advantageously forms said first securing element (or dovetail-shaped female member). Conversely, the intermediate upper face 401 of the intermediate component 400 is advantageously provided with a post 418, which forms said second securing element (or dovetail-shaped male member). As illustrated in FIGS. 16 and 18, said post 418 protrudes from the surface of said intermediate upper face 401 and has a shape and dimensions complementary to those of said groove 311.

Figures 11, 12:
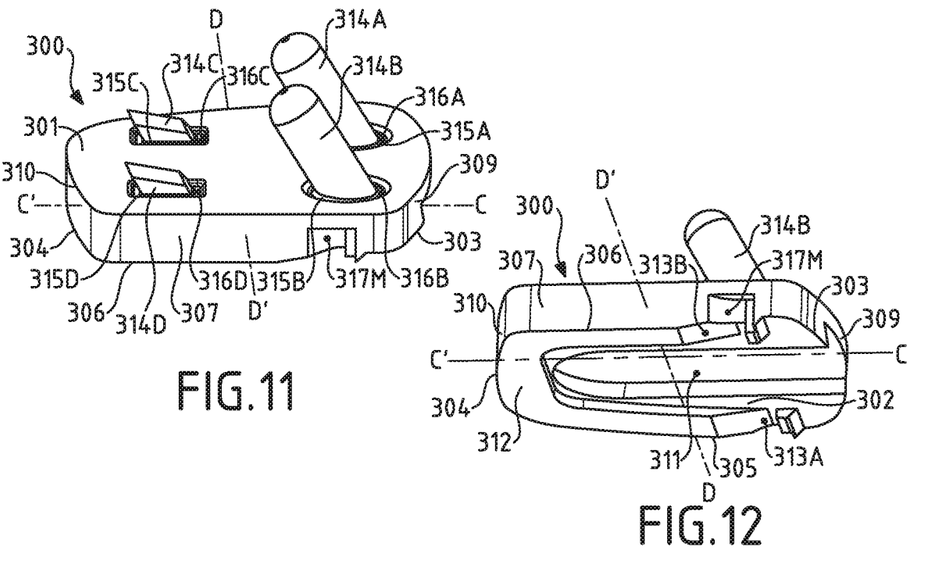
FIGS. 11 and 12 illustrate, respectively according to top and bottom perspective views, the tibial component of the prosthesis of FIGS. 1 and 2.
Figure 13:
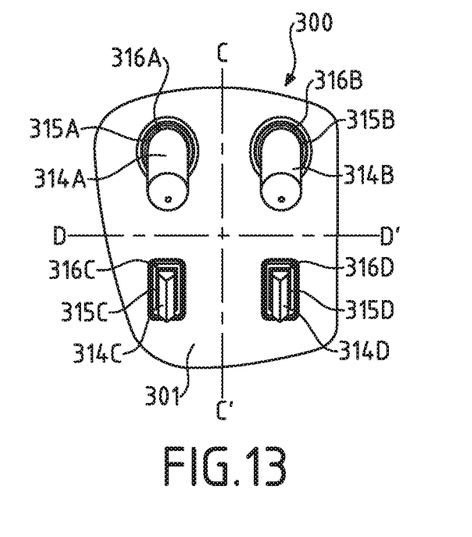
FIGS. 13 and 14 illustrate, respectively in top view and in bottom view, the tibial component of FIGS. 11 and 12.
Figure 14:
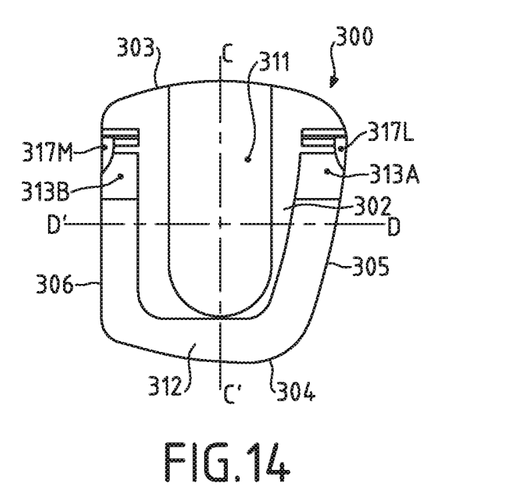
Figure 15:
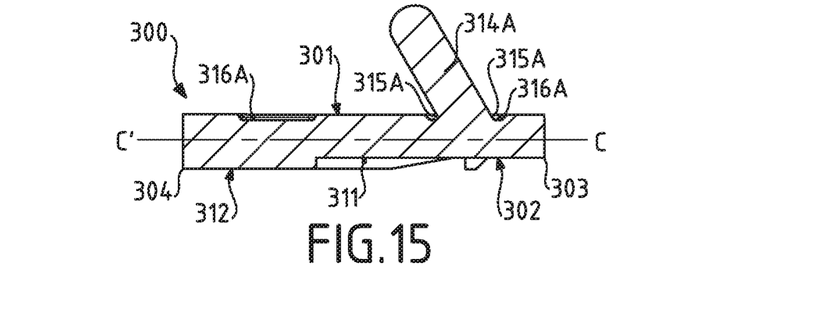
FIG. 15 illustrates, according to an antero-posterior sectional view, the tibial component of FIGS. 11 to 14.

Preferably, said groove 311 extends longitudinally according to said third average direction C-C', from the tibial anterior face 309 of the tibial component 300, at the level of which it opens, towards the tibial posterior face 310, and that on at least over half the average distance which separates said tibial anterior face 309 and tibial posterior face 310 (FIGS. 12 and 14). Advantageously, said post 418 extends longitudinally according to said fifth average direction E-E', from the intermediate anterior face 414 of the intermediate component 400, towards the intermediate posterior face 415 of the latter. Preferably, the length of said post 418 is smaller than the respective length of said groove 311 (FIGS. 16 and 18).

Said groove 311 is thus advantageously designed and configured to receive in a narrow sliding manner said post 418, said tibial lower face 302 and intermediate upper face 401 then being held pressed against each other. Such a relative dovetail assembly thus advantageously allows blocking at least any medio-lateral translation and any rotation of the intermediate component 400 relative to the tibial component 300. Advantageously, said post 418 may be provided, at its posterior end with lateral slopes 419A, 419B (or chamfers) designed to facilitate, guide, the introduction of the post 418 in the groove 311 during the relative assembly of the tibial component 300 and the intermediate component 400.

Of course, a reversed configuration may be considered, said tibial lower face 302 being provided with said post, said intermediate upper face 401 being reciprocally provided with said groove. Any other suitable means for mutual fastening, implementing first and second securing means different from those described hereinbefore, may also be implemented.

Furthermore, it may be advantageously provided that for different sizes of tibial component 300 and intermediate component 400, the dimensions of said groove 311 and of said post 418 are respectively identical. It will then be advantageously possible to propose to the surgeon a prosthetic kit comprising a range of talar 200, tibial 300 and intermediate 400 components, respectively having different sizes to be adapted to the morphology of the patient to be treated, while ensuring the compatibility between a tibial component 300 and an intermediate component 400 which correspond to prostheses of different sizes.

In the preferred case of such a dovetail assembly, said tibial component 300 and intermediate component 400 preferably further comprise respectively complementary first and second stop elements designed to limit or block the antero-posterior translation (that is to say from the front to the rear) of the intermediate component 400 relative to the tibial component 300, said first and second stop elements being advantageously distinct from said first and second complementary securing elements. In other words, the limitation (and preferably the blocking) of the antero-posterior translation is advantageously not ensured (or, at least not exclusively) by the dovetail assembly itself, but by the cooperation of said first and second complementary stop elements. Thus, this advantageously avoids the resumption, by the only groove 311 and post 418, of the mechanical forces applied to the tibial component 300 when the prosthesis 100 is in use.

Preferably, said first and second stop elements comprise respectively a flange 312 positioned at least at the level of the tibial posterior edge 304 of the tibial lower face 302 of the tibial component 300, and a clearance 420 formed at the level of the intermediate upper face 401 of the intermediate component 400 (for example at the level of the first intermediate posterior edge 405) and having a profile complementary to that of said flange 312. Said clearance 420 is thus designed and configured to receive said flange 312, said tibial lower face 302 and intermediate upper face 401 being advantageously in planar contact against each other. The cooperation of said flange 312 and clearance 420 thus limits, and preferably blocks, the antero-posterior travel of the post 418 in the groove 311. Of course, stop elements with a different design might be implemented.

According to the preferred embodiment illustrated in the figures, said flange 312 is positioned at the level of said tibial posterior edge 304, tibial lateral edge 305 and tibial medial edge 306 of the tibial lower face 302 of the tibial component 300, and advantageously extends in a substantially continuous manner along the considered edges 304, 305, 306. Said flange 312 preferably has a rectangular section, which may be constant or not. Conversely, said clearance 420 is preferably formed at the level of the first intermediate posterior edge 405, first intermediate lateral edge 406 and first intermediate medial edge 407 of the intermediate upper face 401 of said intermediate component 400, advantageously in a substantially continuous manner along the considered edges 405, 406, 407.

Thus, the implementation of such advantageously semi-peripheral complementary flange 312 and clearance 420, and their cooperation when the intermediate component 400 is fastened to the tibial component 300, not only allows limiting the risk of shearing of the post 418 in said groove 311, but also advantageously limiting the risk of deformation of the intermediate component 400 by creeping under the effect of the compressive force exerted on the latter by the tibial component 300 in normal use of the prosthesis 100. The service life of the intermediate component 400 is thus substantially improved, which allows limiting the risk of having to proceed with a subsequent surgical operation for replacing the latter.

Preferably, in order to also block any postero-anterior translation (that is to say from the rear to the front) of the intermediate component 400 relative to the tibial component 300, when the latter are fastened to each other, said tibial component 300 and intermediate component 400 are advantageously respectively provided with first 313A, 313B and second 421A, 421B complementary locking means.

As illustrated in FIGS. 12 and 14, said first locking means 313A, 313B may, for example, be in the form of sawteeth-like notches 313A, 313B formed in the flange 312 of the tibial lower face 302, for example symmetrically at the level of the tibial lateral edge 305 and the tibial medial edge 306 of said tibial component 300. Conversely, said second locking means 421A, 421B may, in turn, be in the form, for example, of lugs 421A, 421B having shapes complementary to said sawteeth-like notches 313A, 313B, arranged at the level of the clearance 420 of the intermediate component 400 (FIGS. 16 to 18). The tibial component 300 and the intermediate component 400 may thus be locked to each other by clipping, the local elastic deformation of the material forming the intermediate component 400 allowing the engagement of the lugs 421A, 421B of the latter in the corresponding notches 313A, 313B of the tibial component 300. Of course, other first 313A, 313B and second 421A, 421B suitable complementary locking means may be considered instead of those just described.

Preferably, the tibial component 300 is designed to be removably fastened to the intermediate component 400, in particular in order to authorize the replacement of the intermediate component 400 in case of degradation of the latter (wear, deformation, etc.). In this case, the first 313A, 313B and second 421A, 421B complementary locking means will be designed to authorize a reversible locking of the tibial component 300 and the intermediate component 400 therebetween. As such, the intermediate component 400 might, for example, be provided with recesses 422A, 422B formed in the intermediate upper face 401 in the immediate vicinity of the lugs 421A, 421B forming said second locking means 421A, 421B, and designed to receive the end of an external instrument (not shown, for example a flat screwdriver). The action of this external instrument, for example by lever effect or by rotation, will advantageously allow a local elastic deformation of the material forming the intermediate component 400 and a decoupling of the notches 313A, 313B and lugs 421A, 421B, thus authorizing the disengagement of the talar 300 and intermediate 400 components.

Advantageously, the talar component 200 is provided at the level of its talar lower face 207 with at least one talar anchoring means 216A, designed to ensure the anchoring of the talar component 200 in the bone mass of the concerned talus. Preferably protruding from the talar lower face 207 of the talar component 200, said talar anchoring means 216A is advantageously intended to be housed, during the setup of the talar component 200 in the body of the patient, in a corresponding housing (or hole) practiced beforehand (or during the setup of the talar component 200) by the surgeon in the bone mass of the talus. As illustrated in particular in FIGS. 7 and 9, the talar component 200 is provided with two talar anchoring means 216A, 216B, formed by two talar studs 216A, 216B, for example cylindrical with a rounded head, which protrudes from the talar lower face 207 of the talar component 200. Preferably, said talar studs 216A, 216B extend in an inclined manner, towards the talar posterior edge 204. Of course, other suitable types, shapes and configurations of talar anchoring means 216 might be considered.

In order to ensure an excellent mechanical resistance of said talar anchoring means 216A, in particular to fatigue, the latter is preferably connected to the talar lower face 207, at the level of its base, by a talar fillet 217A, that is to say by a curved surface, or by one or several rib(s). In the preferred embodiment illustrated in the figures, each of the talar anchoring means 216A, 216B is thus advantageously connected to the talar lower face 207 by a respective talar fillet 217A, 217B. However, it has been observed that the presence of such a fillet 217A, 217B may be troublesome during the setup, for example by impaction, of the talar component 200 into the body of the patient, to the extent that such a fillet 217A, 217B then protrudes from the surface of the talar lower face 207. Indeed, the drill bits usually available to make housings in the bone mass do not allow easily making a countersink which might receive the fillet 217A, 217B. The implementation of such a fillet 217A, 217B may be in particular unfavorable in the case, considered hereinbefore, where the talar lower face 207 is provided with a surface coating, since the presence of the latter tends, depending on its thickness, to amplify the importance of said fillet 217A, 217B, and therefore to further impede the setup of said talar component 200.

To overcome this drawback, said talar lower face 207 is advantageously provided with at least one talar cuvette 218A from the bottom of which said at least one talar anchoring means 216A protrudes from said talar lower face 207. In the preferred embodiment illustrated in the figures, said talar lower face 207 is advantageously provided with a plurality of talar cuvettes 218A, 218B from the respective bottom of which said talar studs 216A, 216B protrude from said tibial upper face 301. As illustrated in the figures, said talar cuvette 218A, 218B is advantageously dimensioned so that said fillet 217A, 217B is integrally contained in said talar cuvette 218A, 218B and therefore does not protrude from the surface of the talar lower face 207.

Thus, said talar component 200 may be set up in a relatively simple and accurate manner at the level of the talus, the talar lower face 207 being able to come into perfect surface contact with the corresponding area of the talus, and that without the need for specific tools for drilling the bone mass.

Advantageously, the tibial component 300 is provided at the level of its tibial upper face 301 with at least one tibial anchoring means 314A, designed to ensure the anchoring of the tibial component 300 in the bone mass of the concerned tibia. Preferably protruding from the tibial upper face 301 of the tibial component 300, said tibial anchoring means 314A is advantageously intended to be housed, during the setup of the tibial component 300 in the body of the patient, in at least one housing (or hole) practiced beforehand (or during the setup of the tibial component 300) by the surgeon in the bone mass of the tibia.

As illustrated in particular in FIGS. 11 to 13 and 15, the tibial component 300 is preferably provided with a plurality of tibial anchoring means 314A, 314B, 314C, 314D, for example formed by two cylindrical tibial studs 314A, 314B with a rounded head, which protrude from said tibial upper face 301 in the vicinity of the tibial anterior edge 303, and by two tibial fins 314C, 314D, which protrude from said tibial upper face 301 in the vicinity of the tibial posterior edge 304. Preferably, said tibial fins 314C, 314D have acute and even sharp ridges, to promote their penetration into the bone mass of the tibia. Advantageously, said tibial studs 314A, 314B and said tibial fins 314C, 314D extend in an inclined manner towards the tibial posterior edge 304. The angle of inclination of said tibial studs 314A, 314B and said tibial fins 314C, 314D will be advantageously selected to facilitate the introduction of the tibial component 400 into the body of the patient, and its setup at the level of the tibia of the latter, while limiting the necessary joint distraction. Of course, other suitable types, shapes and configurations of tibial anchoring means 314A, 314B, 314C, 314D might be considered.

Preferably, in manner substantially similar to what has been described hereinbefore in connection with said at least one talar anchoring means 216A of the talar component 200, said at least one tibial anchoring means 314A is preferably connected to the tibial upper face 301, at the level of its base, by a tibial fillet 315A. Said tibial upper face 301 is then advantageously provided with at least one tibial cuvette 316A, from the bottom of which said at least one tibial fastening means 314A protrudes from said tibial upper face 301. In the preferred embodiment illustrated in the Figures, each of the tibial studs 314A, 314B and each of the tibial fins 314C, 314D is thus advantageously connected to the tibial upper face 301 by a respective tibial fillet 315A, 315B, 315A, 315B. Said tibial upper face 301 is then advantageously provided with a plurality of tibial cuvettes 316A, 316B, 316A, 316B from the respective bottom of which said tibial studs 314A, 314B and said tibial fins 314C, 314D protrude from said tibial upper face 301.

Figure 9:
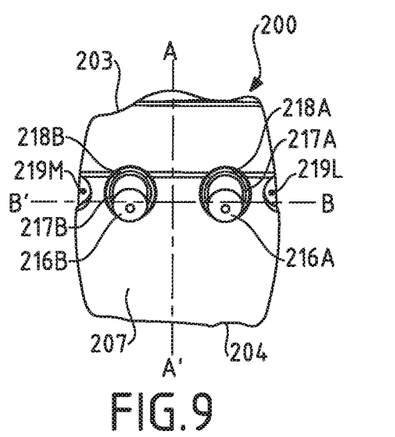
Figure 10:
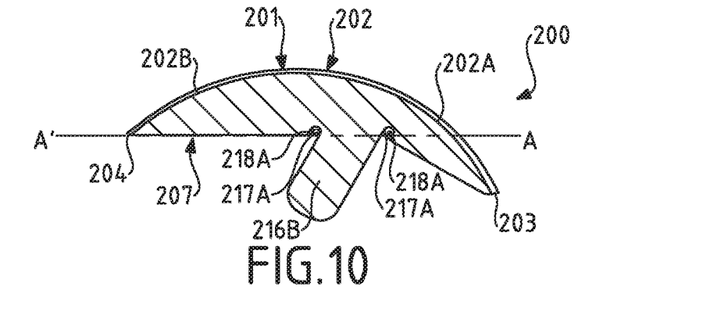
FIG. 10 illustrates, according to an antero-posterior sectional view, the talar component of FIGS. 6 to 9.

As illustrated in FIGS. 7 and 9, the talar lateral edge 205 and the talar medial edge 206 of the talar component 200 are preferably respectively provided with a talar lateral notch 219L and a talar medial notch 219M, advantageously positioned in a symmetrical manner in the vicinity of the talar anterior edge 203. Said talar lateral notch 219L and said talar medial notch 219M are advantageously designed to cooperate with an external instrument (not illustrated, for example a flat screwdriver), in order to allow the ablation of the talar component 200, for example in case of unsatisfactory positioning or in case of medical complication justifying the removal of all or part of the prosthesis 100.

Similarly, the tibial lateral edge 305 and the tibial medial edge 306 of the tibial component 300, might advantageously be provided respectively with a tibial lateral notch 317L and a tibial medial notch 317M, advantageously positioned symmetrically in the vicinity of the tibial anterior edge 303 (FIGS. 11, 12 and 14).

The invention claimed is:

1. An ankle prosthesis (100) comprising a talar component (200) which includes a talar upper face (201) defining a first articular surface (202) and which extends between a talar anterior edge (203) and an opposite talar posterior edge (204) according to a first average direction (A-A'), said first articular surface (202) being curved according to said first average direction (A-A'), said first articular surface (202) comprising a first curved portion (202A) and a second curved portion (202B), each extending according to said first average direction (A-A'), said first curved portion (202A) having a first curvature according to said first average direction (A-A') and said second curved portion (202B) having a second curvature according to said first average direction (A-A'), said prosthesis (100) being characterized in that said first curved portion (202A) and said second curved portion (202B) define respectively an anterior portion and a posterior portion of said first articular surface (202), said first curvature being greater than said second curvature,
wherein both the first and second curved portions (202A, 202B) extend between a talar lateral edge (205) and an opposite talar medial edge (206) of said talar upper face (201),
and wherein the first and second curved portions (202A, 202B) both extend along an entire width of said first articular surface (202) according to a second average direction (B-B'), orthogonal to said first average direction (A-A').

2. The prosthesis (100) according to claim 1, characterized in that said first curvature is constant or variable, whereas said second curvature is constant.

3. The prosthesis (100) according to claim 1, characterized in that said second curved portion (202B) has a surface area larger than the respective surface area of said first curved portion (202A).

4. The prosthesis (100) according to claim 1, characterized in that said first (202A) and second (202B) curved portions of the first articular surface (202) define first and second substantially frustoconical surface fractions.

5. An ankle prosthesis (100) comprising a talar component (200) which includes a talar upper face (201) defining a first articular surface (202) and which extends between a talar anterior edge (203) and an opposite talar posterior edge (204) according to a first average direction (A-A'), said first articular surface (202) being curved according to said first average direction (A-A'), said first articular surface (202) comprising a first curved portion (202A) and a second curved portion (202B), each extending according to said first average direction (A-A'), said first curved portion (202A) having a first curvature and said second curved portion (202B) having a second curvature, said prosthesis (100),
characterized in that said first curved portion (202A) and said second curved portion (202B) define respectively an anterior portion and a posterior portion of said first articular surface (202), said first curvature being greater than said second curvature;
and further characterized in that said first (202A) and second (202B) curved portions of the first articular surface (202) defining first and second substantially frustoconical surface fractions, said first and second surface fractions being respectively derived from first and second fictional cones, having respectively first and second axes of rotation, said first and second surface fractions joining together in a contact plane inclined at an angle of between 10° and 30° towards said talar anterior edge (203) relative to a vertical plane containing said second axis of rotation, said contact plane containing said first and second axes of rotation.

6. The prosthesis (100) according to claim 1, characterized in that said first articular surface (202) comprises:
a talar lateral area (210L), which extends between said talar anterior edge (203) and said talar posterior edge (204) according to said first average direction (A-A'), and between said talar lateral edge (205) and said talar medial edge (206) according to said second average direction (B-B'), said talar lateral area (210L) comprising a first lateral region (211L) of said first curved portion (202A) and a second lateral region (212L) of said second curved portion (202B), and
a talar medial area (210M), which extends between said talar anterior edge (203) and said talar posterior edge (204) according to said first average direction (A-A'), and between said talar lateral area (210L) and said talar medial edge (206) according to said second average direction (B-B'), said talar medial area (210M) comprising a first medial region (211M) of said first curved portion (202A) and a second medial region (212M) of said second curved portion (202B).

7. The prosthesis (100) according to claim 6, characterized in that said first articular surface (202) also comprises a talar central area (210C), which is interposed between said talar lateral area (210L) and said talar medial area (210M), and which comprises a first central region (211C) of said first curved portion (202A) and a second central region (213C) which extends said first central region (211C) and has a third curvature which is greater than said second curvature.

8. The prosthesis (100) according to claim 7, characterized in that said talar central area (210C) has a convex curvature according to said second average direction (B-B'), said talar lateral area (210L) and talar medial area (210M) having respectively a concave curvature according to said second average direction (B-B').

9. The prosthesis (100) according to claim 1, characterized in that the talar component (200) includes a talar lower face (207) opposite to said talar upper face (201) and in that said talar component (200) is provided, at the level of said talar lower face (207), with at least one talar anchoring means (216A), said talar lower face (207) being provided with at least one talar cuvette (218A) from the bottom of which said talar anchoring means (216A) protrudes beyond said talar lower face (207).

10. The prosthesis (100) according to claim 1, characterized in that it comprises a tibial component (300), which includes a tibial upper face (301) and an opposite tibial lower face (302), said tibial lower face (302) extending, on the one hand, between a tibial anterior edge (303) and an opposite tibial posterior edge (304) and, on the other hand, between a tibial lateral edge (305) and an opposite tibial medial edge (306).

11. The prosthesis (100) according to claim 10, characterized in that the tibial component (300) is provided, at the level of said tibial upper face (301), with at least one tibial anchoring means (314A), said tibial upper face (301) being provided with at least one tibial cuvette (316A) from the bottom of which said tibial anchoring means (314A) protrudes beyond said tibial upper face (301).

12. The prosthesis (100) according to claim 10, characterized in that it comprises an intermediate component (400), which is designed to be interposed between said talar component (200) and said tibial component (300), said intermediate component (400) comprising an intermediate upper face (401) and an opposite intermediate lower face (402), said intermediate lower face (402) defining a second articular surface (403) designed to cooperate with said first articular surface (202).

13. The prosthesis (100) according to claim 12, characterized in that said second articular surface (403) comprises an intermediate lateral area (416L), an intermediate medial area (416M) and an intermediate central area (416C), respectively intended to cooperate with said talar lateral area (210L), talar medial area (210M) and talar central area (210C) of said first articular surface (202), said intermediate lateral area (416L) and intermediate medial area (416M) having curvatures respectively matching with the curvatures of said second lateral region (212L) and second medial region (212M) of the second curved portion (202B) of said first articular surface (202), whereas said intermediate central area (416C) has a curvature matching with the curvature of said first central region (211C) of the first curved portion (202A) of said first articular surface (202).

14. The prosthesis (100) according to claim 12, characterized in that said tibial component (300) is designed to be movable relative to said intermediate component (400).

15. The prosthesis (100) according to claim 12, characterized in that said tibial component (300) is designed to be fastened to said intermediate component (400).

16. The prosthesis (100) according to claim 15, characterized in that said tibial component (300) and intermediate component (400) are designed to be fastened to each other by means of respective first and second securing elements according to a dovetail assembly.

17. The prosthesis (100) according to claim 16, characterized in that said tibial component (300) and intermediate component (400) further comprise respectively first and second complementary stop elements designed to limit or block the antero-posterior translation of the intermediate component (400) relative to the tibial component (300), said first and second stop elements being distinct from said first and second complementary securing elements.

18. The prosthesis (100) according to claim 17, characterized in that said first and second stop elements respectively comprise a flange (312) positioned at the level of said tibial posterior edge (304), tibial lateral edge (305) and tibial medial edge (306) of the tibial lower face (302) of the tibial component (300), and a clearance (420) formed at the level of the intermediate upper face (401) of the intermediate component (400) and having a profile complementary to that of said flange (312).

19. The prosthesis (100) according to claim 12, characterized in that said tibial component (300) is designed to be removably fastened to said intermediate component (400).

20. An ankle prosthesis (100) comprising a talar component (200) which includes a talar upper face (201) defining a first articular surface (202) and which extends between a talar anterior edge (203) and an opposite talar posterior edge (204) according to a first average direction (A-A'), said first articular surface (202) being curved according to said first average direction (A-A'), said first articular surface (202) comprising a first curved portion (202A) and a second curved portion (202B), each extending according to said first average direction (A-A'), said first curved portion (202A) having a first curvature and said second curved portion (202B) having a second curvature, said prosthesis (100),
characterized in that said first curved portion (202A) and said second curved portion (202B) define respectively an anterior portion and a posterior portion of said first articular surface (202), said first curvature being greater than said second curvature;
and further characterized in that said first (0202A) and second (202B) curved portions of the first articular surface (202) defining first and second substantially frustoconical surface fractions, said first and second surface fractions being respectively derived from first and second fictional cones, having respectively first and second axes of rotation, said first and second surface fractions joining together in a contact plane inclined at an angle of about 20° towards said talar anterior edge (203) relative to a vertical plane containing said second axis of rotation, said contact plane containing said first and second axes of rotation.

* * * * *